(12) United States Patent
Orrantia Borunda et al.

(10) Patent No.: US 8,859,217 B2
(45) Date of Patent: Oct. 14, 2014

(54) METHOD OF DETERMINING THE SEX OF BIRDS, REPTILES AND MAMMALS USING STEROID HORMONES

(75) Inventors: Erasmo Orrantia Borunda, Chihuahua (MX); Raymundo Rene Rivas Caceres, Chihuahua (MX)

(73) Assignee: Centro de Investigacion en Materiales Avanza Dos S.C. (CIMAV), Chihuahua (MX)

( * ) Notice: Subject to any disclaimer, the term of this patent is extended or adjusted under 35 U.S.C. 154(b) by 1177 days.

(21) Appl. No.: 11/921,963

(22) PCT Filed: Jun. 13, 2006

(86) PCT No.: PCT/MX2006/000051
§ 371 (c)(1),
(2), (4) Date: Dec. 11, 2007

(87) PCT Pub. No.: WO2006/135222
PCT Pub. Date: Dec. 21, 2006

(65) Prior Publication Data
US 2009/0286266 A1    Nov. 19, 2009

(30) Foreign Application Priority Data
Jun. 13, 2005    (MX) .................... NL/a/2005/000051

(51) Int. Cl.
*G01N 33/53*    (2006.01)
*G01N 33/68*    (2006.01)
*A01K 45/00*    (2006.01)
*G01N 33/74*    (2006.01)
*A01K 67/02*    (2006.01)

(52) U.S. Cl.
CPC ............ *G01N 33/743* (2013.01); *G01N 33/689* (2013.01); *A01K 45/00* (2013.01); *A01K 67/02* (2013.01)
USPC ....................................... 435/7.92

(58) Field of Classification Search
None
See application file for complete search history.

(56) References Cited

FOREIGN PATENT DOCUMENTS

CN         1227350 A      9/1999

OTHER PUBLICATIONS

Kubokawa et al. (Zoo. Sci., 9:1017-1023, 1992).*
Tell et al. (Zoo Biol., 10:361-367, 1991).*
Bercovitz et al. (J. Zoo. An. Med, 9:114-124, 1978).*
Lee et al. (Zoo Biol., 14:97-106, 1995).*
DsLabs (product insert for ACTIVE Testosterone EIA, 2004).*
Muir, C. et al. Enzyme Immunoassay of 17B-Etradiol, Estrone Conjugates, and Testoterone in Urinary and Fecal Samples from Male and Female Mice. Hormone and Metabolic Research, 2001, vol. 33, No. 11, pp. 653-658, ISSN 0018-5053.
Testosterone EIA, DSL-10-4000. Datasheet. Diagnostic System Laboratories, Inc. Http:/www.dslabs.com/docs/inserts/10-4000.pdf, 2004.
Garcia Perreira RJ et al. Seasonal changes in fecal testoterone concentration and their relationship to reproductive behavior, antler cycle and grouping patterns in free raging male Pampas derr vol. 63, No. 8, pp. 2113-2125 ISSN 0093-961X, 2005.

* cited by examiner

*Primary Examiner* — Brian J Gangle
(74) *Attorney, Agent, or Firm* — Defillo & Associates, Inc.; Evelyn A. Defillo

(57) ABSTRACT

The present invention consists in the design of an ELISA test, specific to determine through fecal feces, urine or plasma of birds, reptiles and mammals, the levels of concentration of the hormone testosterone as an indicator of masculine sex in these species for a better handling of the reproduction and the production of birds, reptiles and mammals. The procedure can be applied for practical purposes in any commercial operation that involves these species. With this method a greater efficiency and economic return is obtained, which reports improvement and greater benefits to the producers.

2 Claims, No Drawings

METHOD OF DETERMINING THE SEX OF BIRDS, REPTILES AND MAMMALS USING STEROID HORMONES

CROSS REFERENCE TO RELATED APPLICATION

This application is a national stage of PCT/MX2006/000051 filed Jun. 13, 2006 and based upon Mexican Patent Application No. NL/a/2005/000051 filed Jun. 13, 2005, under the International Convention.

FIELD OF THE INVENTION

The main objective of this invention is to determine, through feces or urine from birds, reptiles and mammals, the levels of concentration of the testosterone hormone as a male sex indicator in these classes of vertebrates.

In view of the necessity of making an early determination of sex, with the objective to provide improved reproductive adaptation, since the individuals are very young, to induce an early reproduction and to have a greater production in the breeding places.

BACKGROUND OF THE INVENTION

The interest in the use of monitored fecal steroids as an indicator of the endocrine status has grown considerably in recent years for an ample variety of species. Nevertheless, the success in the application of the basic technique requires the knowledge of the time at which the animal already presents hormonal secretion, as well as the metabolic forms in which these steroids are excreted (time lag).

The time lags are necessary to determine the time between the occurrence of physiological events and its detection in the feces. The knowledge of the metabolic events is critical to maximize the efficiency of the immunoassays used to quantify the feces steroid profiles.

Wasser, S. K; Velloso, A. D. L; Rodden, M. D. 1995. Using fecal steroids to evaluate reproductive function in female maned wolves. Journal of Wildlife Management, v. 59, n. 4:889-894; they made a study that represented the first attempt to apply the measurement of canine feces steroid and suggested that these noninvasive measurements can provide an important tool for the herd wolf pack in danger of extinction.

For this, they measured the estrogen and progestin concentrations during a period of time in the feces of nine female wolves to determine if the measurements can be used to observe their reproductive function. The subjects were located in five zoo parks of the United States of America, two to three samples were collected weekly for a period of 3 to 5 months, beginning just in the period previous to the heat stage.

The measurement of fecal steroid indicated occurrence of ovulation and pregnancy in 8 of the 9 females. The females in cycle showed estrogen presence with the production of progesterone in the luteum phase. This estrogen presence was followed by a maintained production of progestin levels of $27.2\pm2.65$ mu-g/g in conceptive cycles during the next subsequent 63 days (first period of gestation), which was higher than the $7.6\pm0.73$ mu-g/g of the progestin concentration in non-conceptive cycles.

The estrogen concentrations in acyclic young females never reach more than 50 ng/g (nanograms per gram), whereas their values of progestin remained under 3.0 ng/g. The measurements of fecal steroids provide useful means to characterize the fertility, including the ovulation and the pregnancy in female wolves.

Brown, J. L; Wasser, S. K; Wildt, D. E; Graham, L. H. 1994. Comparative aspects of steroid hormone metabolism and ovarian activity in fields, measured noninvasively in feces. Biology of Reproduction, v. 51, n. 4:776-786; used noninvasive fecal tests to study the steroid metabolism, as well as the ovarian activity of several feline species.

Using the domestic cat *Felis catus* as a model, when estradiol (E-2) (14C) and the progesterone (P-4) (14C) were injected, the excreted products were determined. It was found on a two day period activity of $97.0\pm0.6\%$ and $96.7\pm0.5\%$ of E-2 and P-4. E-2 was excreted as non-conjugated estradiol and as estrogen (40%) and also as non-hydrolizable conjugated enzyme (60%). In addition, P-4 was excreted initially as a non-hydrolizable enzyme, as well as non-conjugated epimers of pregnenolone.

In view of the repeated capture and the taking of blood samples, which are generally impractical strategies in the monitoring of the reproductive stratum of wild species, the non-invasive methods to pursue the reproductive activity have been increased significantly.

Wasser, S. K; Thomas, R; Nair, P. P; Guidry, C; Southers, J; Lucas, J; Wildt, D. E; Monfort, S. L. 1993. Effects of Dietary Fibre on Faecal Steroid Measurements in Baboons Papio-Cynocephalus-Cynicephalus. Journal of Reproduction and Fertility, V. 97, n. 2:569-574; used radioimmunoassay (RIA) of pregnanediol-3 alpha glucuronic (PdG) in the urine, conjugated of estrogens, fecal progesterone and estradiol to assure the menstrual cycles and the pregnancy of captive elks.

Using PdG in the urine, different reproductive cycles that began in October were identified when the estral behavior agreed with the maximum level of excretion of PdG. Although this compound increased more than five times over the cyclical levels of the pregnancy, the concentrations were variable making the pregnancy diagnosis incorrect when using this method.

The estrogen conjugated was not useful to monitor the heat cycles; nevertheless, during the last month of gestation, the conjugated estrogen levels in the urine increased less than five nanograms per milligram of Creatinine (Cr) to more than 50 ng per milligram of Cr, making this a useful method for the definitive detection of the delayed pregnancy.

In order to establish a simple pregnancy test, they evaluated estradiol and progesterone in feces (one to six samples per individual), collected over a period of two years, of 16 elks of different ages, kind and physiological classifications, pregnant against non-pregnant.

Using fecal progesterone and blind tests; the technicians correctly identified the status of pregnancy in 22 of the 26 cases (85%) with three false positives and a mistaken diagnosis; fecal estradiol proved to be less effective (15/26) (58%) for the exact diagnosis of pregnancy. These methods have excellent potential to monitor the reproductive activity of elks in captivity and wildlife.

Barney A. Schlinger and Arthur P. Arnold. 1992. Circulating estrogens in a male songbird originate in the brain. Department of Psychology and Laboratory of Neuroendocrinology of the Brain Research Institute. University of California. Los Angeles, Calif.; observed that the gonad steroids act in the brain to regulate the development and expression of the reproductive behavior of vertebrates.

In addition, the steroids controlled in the brain are an integral part of the regulation of the feedback of the steroidogenesis. The actions of androgens in the brain are frequently mediated for the enzymatic activation or inactivation of the circulating hormone, including local conversion of androgen to estrogens.

They reported that the brain synthesizes great amounts of estrogen from androgens and releases the estrogen in the blood, being probable that the brain controls the levels in the plasma of this steroid, when totally contributing with high levels of estrogen found in the circulation.

Barney A. Schlinger and Arthur P. Arnold. 1991. The brain the major site of estrogen synthesis in a male songbird. Department of Psychology and Laboratory of Neuroendocrinology of the Brain Research Institute. University of California. Los Angeles, Calif.; found that the neural system that controls the singing of the birds can experience strong morphologic and functional changes during its development and adult stage and many of these changes are regulated by estrogenic hormones.

High levels of estrogen circulate in the blood of the males in singing birds and is present after the castration. These investigators measured the activity of aromatase, the enzyme that converts androgens in estrogens in several female tissues and adult males and as they had expected, the activity of aromatase was present in the male hypothalamus/preoptic region, the pituitary and the feminine ovary, although the aromatase was unusually active in telencephalon of males and females. On the contrary, the activity was undetectable in adrenal testis or other masculine tissue.

These results suggest that the brain is the source of the circulating estrogens in males and that its action over the singing system results from the local aromatization more than peripheral.

Schlinger and Callard, G. 1987. A comparison of Aromatase, alfa, and 5 beta-Reductase Activities in the Brain and Pituitary of Male and Female Quail (C. c. japonica). The Journal of Experimental Zoology. 242: 171-180; concluded that in numerous species of vertebrates, including the Japanese quail, the actions of the testosterone (T) on the neuroendocrine tissue were mediated in part by the conversion to estrogenic and androgenic metabolic.

The objective was to investigate which processes were favored in each identified androgenic tissue in the brain of the quail and if sexual differences were detected.

These investigators designed a test to quantify simultaneously aromatase $5\alpha$ and $5\beta$-reductase. In addition, they made the first definitive identification of aromatase in the pituitary of the quail and compared the three enzymatic activities of the pituitary of males and females.

The enzymes were measured in homogenized tissues by the conversion of (3H) androstenedion to (3H) estrone, $5\alpha$-androtanedion, and $5\beta$-androtanedion. The activity of aromatase was restricted to the limbic tissue (previous hypothalamus, posterior hypothalamus, septum archistratium), which previously contained dyed nucleus; whereas the hiperestriatum, the cerebellum and the middle brain contained interfollicular nucleus, which were negative to aromatase.

The quail pituitary aromatized androgens to rates equivalent to the posterior hypothalamus or preoptical area (aHPOA). The $5\alpha$ and the $5\beta$-reductase were present in all studied tissues. Aromatase was significantly higher in aHPOA and in addition it was present in the pituitary of males, whereas $5\alpha$-reductase was significantly higher in the pituitary of the females.

This data suggests that a metabolic androgen complex of enzymes controls the neuroanatomic distribution (space) of the active hormone in the neuroendocrine tissue, and that the quantitative differences between males and females can serve to differentiate the behavior from sexes.

For the complete expression of testosterone T in the brain and in the peripheral tissue, the circulating hormone is transformed in situ to a metabolite that is biologically more active, for which three metabolic processes in the brain have been identified.

The aromatization and reduction $5\alpha$ lead to the synthesis of estradiol-$1\beta$ and $5\alpha$-dihidrotestosterone respectively. Each one of these metabolites is united to a separated receptor system and has unique actions in the brain in the process of sexual differentiation, sexual behavior and secretion of the pituitary hormone. For example, in the adult of the Japanese quail (*Coturnix coturriii japonica*), the aromatization of androgens to estrogens seems to be essential in the male mating behavior, the aggressiveness and the locomotive activity. Whereas the testosterone, per se, and the androgens $5\alpha$ stimulate the singing and swagger.

The third process of the $5\alpha$ reductase is presumed because of the inactivation that leads the $5\beta$-DHT production (dihidrotestosterone) which does not have a mechanism of demonstrated biological activity in the brain or the pituitary. Wada. M. 1984. Effects of ventricularly implanted sex steroids on calling and locomotor activity in castrated male Japanese quail. Horm. Behav. 18:130-139.

Benjamin et al. 2002. Method For Sex Determination of Mammalian offspring. U.S. Pat. No. 6,489,092 B1. In this a work that is close to the present invention, which is directed towards a method to increase the percentage of descendants of one or another sex in mammals, by the contact of a spermatozoid sample with a specific antibody corresponding to the sex that is wanted to select, the antibody is united to a magnetic sphere of a diameter that produces the separation of a spermatozoid that has the sufficient motility to allow the insemination and the fertilization in a successful way.

Another invention that is related is: Malecha et al. 2004 Methods of Isolating the Androgenic sex Hormone From Crustacean Prawn and Marine Shrimp and Methods of Use. U.S. Pat. No. 6,740,794 B1.

This is a technique for the secretion in vitro of androgenic hormone (AH) of androgenic gland (AG) of the fresh water male shrimp in defined culture medium. One found that AH can be used in the manipulation of the shrimp reproductive process for the production of individuals of a determined sex, that is to say monosexual progeny.

SUMMARY OF THE INVENTION

The present invention comprises selecting a polypeptide of AH in the shrimp. According to this, a method was developed to produce a polypeptide that forms part of the androgenic hormone (AH), from the androgenic gland (AG) cultivated in vitro, additionally methods for the extraction and purification of the androgenic hormone were proven (AH).

DETAILED DESCRIPTION OF THE INVENTION

It is necessary to determine sex in birds, reptiles and mammals at an early age (Youth), in order to have a correct reproductive handling of these species, which would help to establish a more efficient production system, which would result in reproductive and economic benefits for the producers.

For example, the sale of crocodile skins and lizard for the international fur industry, requires the fulfillment of the national and international legislations, each day more strict, on conservation of species in extinction danger, so is being necessary to verify that the sacrificed animals are only males, with the purpose of giving a sustainable development to the handling of this species.

Another example is singing bird breeders, such as canaries, toucans, macaws and parrots, which are required to make sure that only males are sold, which are those that really sing, and where the differentiation of sex in these species in young age is very difficult to determine, reason why the present approach to differentiate the sex in these birds is slow, with a low percentage of effectiveness and can cause the death of some animals due to the manipulation of which they are subjected. With the method described in the present invention these problems are prevented.

Likewise, there is the example of some mammals, in particular the wild species that are in danger of extinction, in which the investigator does not already have to remain in the field during long periods of time observing the wild fauna to determine the sex of the population, since with the present invention the sex can be differentiated without having to manipulate the animal (noninvasive method), or causing any disturbance to the animal, simply collecting fecal feces to determine the number of males and females.

This method is very convenient for its application in commercial operations and the studies in wild fauna, since it is a practical procedure, economical, simple and highly reliable (85%). By the fact that the concentrations of testosterone in fecal feces and urine manifest on an almost exact way, it is possible to define to which sex belongs at any time with any studied specimen.

In commercial breeding places, to know to which specimen (male or female) the feces or urine to be studied belongs, they are confined temporarily in individual cages, which produces a high reliability in this specific method in identifying the sex of a particular manner for each individual.

It is considered that this application can also be used as a pocket "kit", to perform the sex determination in situ, in a fast manner, efficient and reliable.

Next a detailed description is made of the methodology that was followed in the design of the technique of the present invention.

A) Feces
1.—Dissolve 0.5 g to 1.0 g of fecal feces in 1 mL of distilled water, with mechanical agitation (with a vortex) during 5 min. The extraction efficiency can be improved if left during all night.
2.—Add from 3 to 5 mL of ethyl acetate and shake in vortex for 5 min. It is also possible to use diethyl ether.
3.—Place the tubes in dry ice and ethanol to freeze the aqueous phase and decant the organic phase to another tube.
4.—Determine the number of cells (microwells) covered necessary for standards, controls and serum problem, making the tests in duplicate for greater precision.
5.—Place between 5 to 10 microliters (μL) of standards, samples and controls in appropriate microwells.
6.—Add between 50 and 100 μL of conjugated Testosterone-HRP to each microwell.
7.—Add from 25 to 50 μL of rabbit anti-testosterone reagent in each microwell. Gently mix per 30 seconds; it is very important to mix completely. Place the plates inside a plastic bag.
8.—Incubate at 37° C. per 90 minutes with the purpose of drying by evaporation.
9.—Wash five times with distilled or de-ionized water (not to wash abruptly or with tap water).
10.—Add between 50 and 100 μL of TMB in each microwell and agitate per 5 seconds.
11.—Incubate at room temperature by 20 minutes.
12.—Slow the reaction by adding between 50 and 100 μL of stop solution, to stop the reaction of peroxidase in each microwell. This solution is prepared with 1% sodium hydroxide, which causes a higher pH, changes the conformation of the enzyme, inactivating it in view that it no longer has an active site to recognize the specific substrate on which it was acting.
13.—Gently shake per 30 seconds. It is very important to make sure that each microwell of blue color turns completely to yellow color.
14.—Read the absorbance at 450 nm in a microreader within 15 minutes.

B) Urine and/or Plasma
1—Extract between 100 and 200 μL or more and mix with 2 mL of diethyl ether for 5 minutes.
2.—Place tube in dry ice with ethanol to freeze the aqueous phase and decant the organic phase to another tube.
3.—Dry by evaporation.
4.—Resuspend between 150 and 250 μL of methanol.

This procedure serves to identify, in a preliminary way in the organic phase, the testosterone presence.

In order to know to what specimen (male or female) the studied feces or urine belong in the breeding place, they are temporarily confined in individual cages, which produces a high reliability in this specific method in identifying the sex of a particular manner-for each individual.

The experimental design for the ELISA test (Enzyme Linked Immunological Sorbant Assay) is described next:
1—Make a chart of what is going to be on each well of the plate. As is indicated next:

|  | Anti-testo | Anti-Estradiol | Second Antibody |  |
|---|---|---|---|---|
| Sample | + | − | + | 3 wells |
| Sample | − | + | + | 3 wells |
| Sample | − | − | + | 3 wells |
| Methanol Alone | + | − | + | 3 wells |
| Methanol Alone | − | − | + | 3 wells |
| Methanol Alone | − | − | + | 3 wells |

25 to 50 μL of simple or methanol per well.

It is necessary to test each sample with anti-testosterone as well as with anti-estradiol to be able to compare which reaction is stronger. It is required to include control without the first antibody to know if there is any nonspecific reaction of the second antibody. Methanol alone indicates if the antibodies stick indistinctly to the plate.

In addition, estradiol standards and testosterone (positive controls) must be included in the test, to be sure that the antibodies are working and to have an idea of the concentration of hormones in the sample. Example: 25 μL for each one of the solutions 0.2, 2, and 20 ng/ml of testosterone and 10, 100 and 1000 pg/mL of estradiol.

A minimum of 2 wells of each concentration is prepared, to be able to prove the concentration of each hormone with antibodies. Example:

|  | Anti-Testosterone | Anti-Estradiol |
|---|---|---|
| Estradiol 10 pg/mL | + | − |
| Estradiol 10 pg/mL | − | + |
| Estradiol 10 pg/mL | + | − |
| Estradiol 10 pg/mL | − | + |
| Estradiol 10 pg/mL | + | − |
| Estradiol 10 pg/mL | − | + |

2.—Place the samples in the wells and let them dry.
3.—Place 100 µL of blocking solution in each well.
Blocking solution: PBS-TWEEN® (PBST)+2% powdered milk (nonfat dry milk)
Per liter: NaCl . . . 8 g
KCl . . . 0.2 g
$Na_2HPO_4$ . . . 41.44 g
$KH_2PO_4$ . . . 40.24 g
Adjust the pH to 7.4 with HCl o NaOH and add 0.5 mL of TWEEN®-20.
4.—Incubate 1-2 hours at room temperature or overnight at 4° C. Cover with "plastic wrap" to avoid evaporation. Avoid the cross contamination between wells.
5.—Wash 3 times with 200 µL of PBST c/u (vacuum suck if possible).
6.—Add 50 µL per well of the first antibody (previously diluted) 1:10 with PBST and cover and incubate overnight at 4° C. or one hour at 37° C.
7.—Remove the liquid and wash 3 times with 100 µL of PBST in each wash.
8.—Add 50 µL of the second antibody per well, previously diluted 1:1000 in PBST and to incubate one hour at 37° C.
9.—Wash 3 times with 200 µL of PBST in each wash, then wash twice with distilled water.
10.—Add 100 µL of the solution with substrate and incubate to room temperature until the color develops well.
Solution with substrate:
20 mL de 0.05 M of citric acid having adjusted pH to a 4.0 with 1.0M NaOH.
4.4 mg of ABTS.
36 µL of 30% $H_2O_2$ (Add just before to be used).

The ELISA test was used with the positive and negative controls with anti-testosterone, anti-estradiol and second antibody with the purpose of identifying the presence of testosterone in each one of the samples.

The invention claimed is:

1. A kit to determine the sex of birds, reptiles and mammals in situ, the kit comprising:
a case including:
a vial with diethyl ether;
microwells;
a vial with testosterone horseradish peroxidase conjugate (testosterone-HRP);
a plurality of vials including different concentrations of testosterone standards;
a vial including a rabbit anti-testosterone antibody;
a vial including a tetramethylbenzidine (TMB);
a vial including a phosphate buffered saline-polysorbate (PBS-Polysorbate).

2. A method to determine sex in birds, reptiles and mammals, wherein the method is carried out using feces of youth animals, the method consisting of the following steps in the following order:
a) dispersing and agitating the feces of the youth animal in water;
b) adding ethyl acetate or diethyl ether and shaking;
c) freezing the mixture and decanting an organic phase;
d) providing microwells of an appropriate number;
e) coating each microwell with antibodies against rabbit immunoglobulin;
f) placing the mixture into the microwell;
g) adding conjugated testosterone horseradish peroxidase conjugate (testosterone-HRP) to each microwell;
h) adding rabbit anti-testosterone antibodies to each microwell,
i) incubating to dry;
j) washing several times;
k) adding tetramethylbenzidine (TMB) and agitating;
l) incubating at room temperature;
m) slowing the reaction by adding a buffered saline-polysorbate (PBS-Polysorbate)+2% powdered milk;
n) shaking until each microwell changes color;
o) determining the concentration of testosterone by reading the absorbance at 450 nm;
p) repeating steps a) to n) using rabbit anti-estradiol antibodies instead of rabbit anti-testosterone antibodies and determining the concentration of estradiol in step o) instead of the concentration of testosterone;
q) comparing the concentration of testosterone in step o) with the concentration of estradiol in step p) to determine which concentration is stronger;
r) determining the sex of the animal based on the stronger concentration of step q).

* * * * *